(12) United States Patent
Fieselmann et al.

(10) Patent No.: US 12,633,395 B2
(45) Date of Patent: May 19, 2026

(54) METHOD AND DEVICE FOR AUTOMATICALLY DETERMINING SPINE DEFORMATION FROM AN IMAGE

(71) Applicant: Siemens Healthineers AG, Forchheim (DE)

(72) Inventors: Andreas Fieselmann, Erlangen (DE); Zhigang Peng, Ambler, PA (US)

(73) Assignee: SIEMENS HEALTHINEERS AG, Forchheim (DE)

( * ) Notice: Subject to any disclaimer, the term of this patent is extended or adjusted under 35 U.S.C. 154(b) by 451 days.

(21) Appl. No.: 17/943,309

(22) Filed: Sep. 13, 2022

(65) Prior Publication Data

US 2023/0083501 A1 Mar. 16, 2023

(30) Foreign Application Priority Data

Sep. 16, 2021 (EP) ...................................... 21197214

(51) Int. Cl.
*G16H 30/20* (2018.01)
(52) U.S. Cl.
CPC ................................... *G16H 30/20* (2018.01)
(58) Field of Classification Search
CPC ................................................. A61B 17/1671
See application file for complete search history.

(56) References Cited

U.S. PATENT DOCUMENTS 10,970,426 B2 * 4/2021 Mosnier .................. A61B 34/10
2019/0099221 A1 4/2019 Schmidt et al.

2019/0262609 A1 * 8/2019 Brill .................... A61N 1/36071
2019/0347791 A1 11/2019 Fieselmann
2021/0201483 A1 7/2021 Mosnier et al.
2022/0254018 A1 * 8/2022 Zhang .................. A61B 5/0077

FOREIGN PATENT DOCUMENTS

CN 108573502 B 7/2021
CN 113850763 A * 12/2021 ............. G06N 3/045
CN 112365438 B * 2/2024 ............. G06N 3/045

(Continued)

OTHER PUBLICATIONS

Chen, Bo et al: "An Automated and Accurate Spine Curve Analysis System"; IEEE Access; vol. 7, Aug. 29, 2019 (Aug. 29, 2019), pp. 124596-124605, XP011745237.

(Continued)

*Primary Examiner* — Di Xiao
(74) *Attorney, Agent, or Firm* — Harness, Dickey & Pierce, P.L.C.

(57) ABSTRACT

A method for automatically determining spine deformation from an image showing a number of vertebrae of the spine, comprises: detecting center points of the number of vertebrae shown in the image; constructing a center line based on the center points; computing a local tilt at points along the center line; determining positive and negative tilt-maxima of the local tilt and selecting two reference vertebrae having center points closest to the positive and negative tilt-maxima; segmenting an upper endplate of the cranial reference vertebra; segmenting a lower endplate of the caudal reference vertebra; computing an angle between the upper endplate and the lower endplate; and outputting the angle.

23 Claims, 5 Drawing Sheets

(56)                References Cited

FOREIGN PATENT DOCUMENTS

KR          102383857 B1 *   5/2020    ............... A61B 6/00
WO     WO-2020199694 A1 *  10/2020   ........... A61B 5/1071

OTHER PUBLICATIONS

Jefries B:F: et al. (1980), "Computerized measurement and analysis of scoliosis: a more accurate representation of the shape of the curve", 1980, vol. 134, No. 2.

Stokes, A. F. Ian: "Three-dimensional terminology of spinal deformity. A report presented to the Scoliosis Research Society by the Scoliosis Research Society Working Group on 3-D terminology of spinal deformity"; Spine; vol. 19, No. 2, pp. 236-248, Jan. 15, 1994 (Jan. 15, 1994), XP055892878.

Yaling, Pan et al: "Evaluation of a computer-aided method for measuring the Cobb angle on chest X-rays"; European Spine Journal, Springer Berlin Heidelberg, Berlin/Heidelberg; vol. 28, No. 12, Aug. 24, 2019 (Aug. 24, 2019), pp. 3035-3043, XP036932292.

Takahashi T. et al. (2019), Full-spine radiographs: what others are reporting—a survey of Society of Skeletal Radiology members, Skeletal Radiology vol. 48, pp. 1759-1763.

Khanal, Bidur et al: "Automatic Cobb Angle Detection Using Vertebra Detcetor and Vertebra Corners Regression"; Computer Vision—ECCV 2020 : 16th European Conference, Glasgow, UK, Aug. 23-28, 2020 : Proceedings; Part of the Lecture Notes in Computer Science; ISSN 0302-9743; [Lecture Notes in Computer Science; Lect.Notes Computer], Springer International PU, Feb. 1, 2020 (Feb. 1, 2020), XP047535040.

Cai Y. et al (ed.) (2020), "Computational Methods and Clinical Applications for Spine Imaging", https://doi.org/10.1007/978-3-030-39752-4.

Dubost, Florian et al: "Automated Estimation of the Spinal Curvature via Spine Centerline Extraction with Ensembles of Cascaded Neural Networks"; arxiv.org, Cornell University Library, 201 Olin Library Cornell University Ithaca, NY 14853; Nov. 4, 2019 (Nov. 4, 2019), XP081524959.

Bonanni P. (2017), "Contour and Angle-Function Based Scoliosis Monitoring: Relaxing the Requirement on Image Quality in the Measurement of Spinal Curvature", International Journal of Spine Surgery Jan. 2017, 11 (3) 22; DOI.

Konieczny et al. (2012), "Epidemiology of adolescent idiopathic scoliosis", https://dx.doi.org/10.1007%2Fs11832-012-0457-4 Stand: Jul. 24, 2020.

Zhiqiang, Tan et al: "An Automatie Seoliosis Diagnosis and Measurement System Based on Deep Learning"; 2018 IEEE International Conference on Robotics and Biomimetics (ROBIO), IEEE, Dec. 12, 2018 (Dec. 12, 2018), pp. 439-443, XP033529753.

Hayashi K. (1996), "Computational Biomechanics", Springer Science & Business Media, Jun. 12, 2012—277 Seiten.

Bernstein Peter et al: "Radiographie seoliosis angle estimation: spline-based measurement reveals superior reliability eompared to traditional COBB method"; European Spine Journal, vol. 30, No. 3, Aug. 27, 2020 (Aug. 27, 2020), pp. 676-685, XP037412275.

Wald and Wortler (2011), Measurements and Classifications in Musculoskeletal, https://dx.doi.org/10.1055/b-004-134458.

Cobb (1948), "Outline for the study of scoliosis", The American Academy of Orthopedic Surgeons Instructional Course Lectures. vol. 5. Ann Arbor, MI: Edwards, Only abstract available.

* cited by examiner

Clinical Cobb angle in frontal plane [deg.]

1

METHOD AND DEVICE FOR AUTOMATICALLY DETERMINING SPINE DEFORMATION FROM AN IMAGE

CROSS-REFERENCE TO RELATED APPLICATION(S)

The present application claims priority under 35 U.S.C. § 119 to European Patent Application No. 21197214.6, filed Sep. 16, 2021, the entire contents of which are incorporated herein by reference.

FIELD

One or more example embodiments of the present invention pertain to a method and a device for automatically determining spine deformation from a (medical) image, especially an X-ray image, wherein the image shows a number of vertebrae of the spine. Especially, one or more example embodiments of the present invention pertain to an automated measurement of spinal curvature in images combining center line tilt and endplate orientation.

BACKGROUND

Deformities of the spine are a common clinical case. For example, adolescent idiopathic scoliosis (AIS) is a spinal deformity that occurs in growing children and has a prevalence of approximately 0.5% to 5% (depending on the study and country). Measurements of the curvatures of the spine on X-rays are frequently performed for diagnosis and monitoring of treatment response.

The Cobb angle constitutes the gold standard and most frequently performed curvature measurement in the coronal plane (see e.g. Takahashi et al. (2019) "Full-spine radiographs: what others are reporting-a survey of Society of Skeletal Radiology members", Skeletal Radiology volume 48, pages 1759-1763). It was introduced in 1948 (see Cobb (1948) "Outline for the study of scoliosis", The American Academy of Orthopedic Surgeons Instructional Course Lectures. Vol. 5. Ann Arbor, MI: Edwards) and has the advantage that it is easy to perform by a human on an X-ray image.

Yet is has been shown that the Cobb angle is a good measure of the curvatures of the spine. However, it depends on the local endplate orientation and neglects important parts of the curve characteristics, e.g., global spinal curvature and apical vertebra translation (see Bernstein et al. "Radiographic scoliosis angle estimation: spline based measurement reveals superior reliability compared to traditional COBB method", European Spine Journal (2021) 30:676-685).

From a physician's perspective the following pain points exist in Cobb angle measurements:
a) The measurements are subjective and significant inter/intra-reader variability exists. This can be particularly important for follow-up imaging exams. A systematic or random bias in the measurements can affect the clinical decision.
b) Measurement errors can occur.
c) It is time-consuming and unattractive to do these measurements.

In clinical routine, the Cobb angle is measured manually either using the standard measurement tools of the Picture Archiving and Communication System (PACS) or with specialized Cobb angle software measurements tools, which make manual measurement faster compared to using the standard tools.

Besides the manual measurements, there are two main concepts to automate Cobb angle/spinal curvature measurements described in the literature. None of these approaches is yet known to be commercially available.

Concept 1 pertains to automatically calculating Cobb angles based on the detected vertebral upper/lower endplates. The idea of this concept is to automatically find the vertebral upper and lower endplates and perform the Cobb angle measurement. This concept reproduces the traditional Cobb angle measurement. In recent years, (deep) machine learning has been employed in research works to find the endplates and compute the Cobb angle this way (see e.g. Cai et al (ed.) (2020), "Computational Methods and Clinical Applications for Spine Imaging", https://doi.org/10.1007/978-3-030-39752-4).

Concept 2 pertains to automatically calculating spinal curvatures based on the detected spinal centerline. In this approach the spinal curvature is determined by finding the vertebral center points, constructing a smooth center line through the center points and using the curvatures of the centerline to determine Cobb-angle-like angles.

Mathematically, this involves computing an "angle function" (the tilt of the center line vs. the horizontal line at every height point) and taking the negative and positive maxima as reference points for the measurement. This concept is sometimes referred to as the "analytical Cobb angle" (see Stokes (1994) "Three-dimensional Terminology of Spinal Deformity. A Report Presented to the Scoliosis Research Society by the Scoliosis Research Society Working Group on 3-D Terminology of Spinal Deformity", Spine, 19(2):236-48). It is not easy to perform this measurement manually. However, it can be supported by using a computer program as was suggested already in the 1980s (Jeffries et al. (1980), "Computerized measurement and analysis of scoliosis: a more accurate representation of the shape of the curve").

SUMMARY

It is at least one object of one or more example embodiments of the present invention to improve the known systems, devices and methods to facilitate an improvement in determining spine deformation from an image.

At least this object is achieved by a method and a device according to one or more example embodiments of the present invention.

One or more example embodiments of the present invention provide a method for automatically determining (calculating/quantifying) spine deformation from an image (e.g. an X-ray image), wherein the image shows a number of vertebrae of the spine, especially at least the vertebrae S1 to C7. The method comprises the following steps:
a) detecting the center points of vertebrae shown in the image,
b) constructing a center line based on the detected center points,
c) computing a local tilt (e.g. a tilt angle) at points along the center line,
d) determining the positive and negative tilt (angle) maxima of the local tilt (angle) and select two reference vertebrae having their center points closest to the determined tilt (angle) maxima,
e) segmenting an upper endplate of the cranial reference vertebra,
f) segmenting a lower endplate of the caudal reference vertebra, g) computing an angle between the upper and lower endplates of the reference vertebrae and outputting this angle.

An image is needed for the method. This (medical) image must show the vertebrae examined by the method and is especially am image recorded with a technique to visualize bones in a body, e.g. an X-ray image or a CT- or MRI-image.

First, the center points of (the) vertebrae shown in the image are determined. It is not necessary to detect the center points of all vertebrae, but of at least of a plurality of (especially adjacent) vertebrae. The more center points of different vertebrae are determined the better is the result. Since types of deformations are known by a physician and the relevant vertebrae for these types are also known, at least the center points of the relevant vertebrae for a predefined type of deformation should be determined.

The determination of the center points is preferably accomplished automatically. This is preferably realized by segmenting the image by recognizing the vertebrae in the image as image-objects and then calculating the center point of each recognized image object (vertebra). This can be achieved by a programmed algorithm or by a trained machine learning algorithm that has been trained to recognize vertebrae in the image and especially also to determine their center points. General machine learning algorithms that are able to recognize vertebrae in an image and able to determine their center points are known in the art. Also the endplates of the vertebrae could be segmented by this algorithm. A preferred model could detect all 4 corner points of each vertebra and then define endplates, wherein the upper endplate is the line spanned by the two upper corner points and the lower endplate is the line spanned by the two lower corner points. The center is defined as the center of all four corner points.

After the center points are known, the center line is constructed, preferably with the use of splines, based on the detected center points. It is preferably constructed by leading a smooth line through all determined center points (following the spine). Here it can be seen that it is advantageous to determine the center points of many (especially all) vertebrae shown in the image, at least of all vertebrae between two selected vertebrae (e.g. S1 and C7), since otherwise the center line would pass some vertebrae with non-determined center points.

Then, the local tilt of points along the center line is calculated, e.g. by using the first derivative, especially derived in respect to the Z-axis (vertical length of the spine). Also a normal course of the spine could be compared with the center line and a deviation of the center line from this normal course (as reference) could be calculated and then the tilt of points could be determined relative to the normal course, e.g. by calculating a gradient. It should be noted that here not the deviation itself is relevant, but the tilt of the points of the center line.

Looking at this calculated local tilt, the positive and negative tilt-maxima of the center line are determined, i.e. the points with the largest tilt in one direction (positive) and in the opposite direction (negative), concerning the course of the center line. Since the first deviation is a measure for the tilt, positive and negative maxima of the first deviation could be taken as tilt-maxima. In the case, there is a plurality of positive or negative local maxima, it is preferred to take the largest maximum as tilt-maximum.

Then, two reference vertebrae are selected. The reference vertebrae are those two vertebrae having their center points closest to the determined tilt-maxima. It should be noted that one reference vertebra is closest to the positive tilt-maximum and the other reference vertebra is closest to the negative tilt-maximum.

Now, the endplates of the far sides of the reference vertebrae are segmented (upper endplate of the cranial vertebra and lower endplate of the caudal vertebra). With the segmentation, their lateral position and their orientation (tilt angle) is determined.

The endplates could be defined by landmarks (e.g. the corners of the vertebra or points along the vertebral body contour). The above mentioned algorithms (conventional or trained) could be used to segment the endplates of the vertebrae, however, it is preferred to use a different algorithm.

Again, the determination of said endplates is preferably accomplished automatically. This is preferably realized by defining the respective endplates of the far sides of the reference vertebrae (preferably by using the above determined image-objects) and then calculating the plane of the endplate. This can, again, be achieved by a programmed algorithm or by a trained machine learning algorithm that has been trained to recognize endplates of vertebrae in the image. General machine learning algorithms recognizing endplates of vertebrae in an image are known in the art. It is preferred to detect the corner points and define the endplate as a line running through the corner points. Alternatively, it is preferred to find the vertebral contour and define the endplate being a part of this contour (cranial or caudal side).

There could be used one single algorithm to recognize/determine the endplates, or there could be used one algorithm to segment the upper endplate of the cranial reference vertebra and another algorithm to segment the lower endplate of the caudal reference vertebra.

Last, the angle between these two endplates of the reference vertebrae is calculated (automatically). In general, methods for the automatic calculation of an angle between two endplates are well known in the art.

This method shows a possibility for automatically determining a Cobb-angle-like angle based on an (e.g. X-ray) image to eliminate the physician's pain points indicated in the introducing part. In the first part of the method, the local tilt (angle) of the spinal centerline is used to determine the reference vertebrae for the angle measurement. In the second part of the method, the upper and lower vertebral endplates of two vertebrae (the reference vertebrae) are used to compute the angle. It is noted that here technically no Cobb angle is determined (in the traditional way), since not all endplates are considered here, but the spinal center line.

One or more example embodiments provide a device for automatically determining spine deformation from an image showing a number of vertebrae of the spine is preferably designed to perform the method according one or more example embodiments of the present invention. The device comprises the following components:

a center-point unit designed for detecting the center points of a number of vertebrae shown in the image, a center-line unit designed for constructing a center line based on the detected center points, a line-tilt unit designed for computing a local tilt (e.g. a tilt angle) at points along the center line, a max-min unit designed for determining the positive and negative tilt (angle)-maxima of the local tilt (angle) and select two reference vertebrae having their center points closest to the determined tilt (angle)-maxima.

a segmentation unit designed for segmenting an upper endplate of the cranial reference vertebra, and designed for segmenting a lower endplate of the caudal reference vertebra, an angel-determination unit designed for computing an angle between the upper and lower endplates of the reference vertebrae and outputting this angle.

While the technical function of the units can be derived from the description of the method, it should be noted that the segmentation unit could use one single algorithm for segmenting both endplates or an individual algorithm for each endplate, wherein an algorithm is preferably a neural network.

It should be noted that in contrast to the prior art, the angle is determined based on the tilt of the endplates, wherein the reference vertebrae comprising these endplates are chosen based on the local tilt (angle) of the centerline. Thus, one or more example embodiments of the present invention combine individual benefits of methods of the prior art.

A key advantage of using the center line to determine the spinal curvature angle is that this method is more robust against limited X-ray image quality. Image quality can be limited by factors such as non-optimal exposure settings, patient movement, foreign objects and overlapping anatomical structures. In these cases, finding the endplates orientations may be challenging especially under pathological spinal conditions. Using the center line to determine the curvature is generally robust against outliers in individual endplate orientations.

A key advantage of using the vertebral endplates for the measurement of the spinal curvature angle is that these landmarks are used in the normal measurement procedure for the Cobb angle. This would increase acceptance and usefulness of the measurement in the clinical routines.

Some units or modules of the device mentioned above can be completely or partially realized as software modules running on a processor of a computing system. A realization largely in the form of software modules can have the advantage that applications already installed on an existing system can be updated, with relatively little effort, to install and run these units of the present application. An object of one or more example embodiments of the present invention is also achieved by a computer program product with a computer program that is directly loadable into the memory of a computing system, and which comprises program units to perform the steps of the inventive method when the program is executed by the computing system. In addition to the computer program, such a computer program product can also comprise further parts such as documentation and/or additional components, also hardware components such as a hardware key (dongle etc.) to facilitate access to the software.

A computer readable medium such as a memory stick, a hard-disk or other transportable or permanently-installed carrier can serve to transport and/or to store the executable parts of the computer program product so that these can be read from a processor unit of a computing system. A processor unit can comprise a microprocessor or its equivalent.

Particularly advantageous embodiments and features of the present invention are given by the dependent claims, as revealed in the following description. Features of different claim categories may be combined as appropriate to give further embodiments not described herein.

According to a preferred method, the image comprises a view on the coronal and/or sagittal plane of a patient, and is preferably an X-ray image, a computed tomography (CT)

image, an ultrasound image or a magnetic resonance (MR) image. It especially comprises multi-planar reformatted slices when the image is of tomographic nature.

It should be noted that also 3D images could be used and the angle between the endplates could be determined in 3D-space. However, in clinical praxis, typically angles in the coronal plane or the sagittal plane are used for diagnosis. Thus, in the case of a 3D image, e.g. an CT- or MR-image even if it comprises a pile of slices, it is first reduced to a 2D image showing the sagittal plane or the coronal plane before applying the method according to one or more example embodiments of the present invention. At least, when applying the method to a 3D image, it is preferred that the angle is calculated in the coronal or sagittal plane, only, especially as well as the geometric condition of the endplates and particularly as well as the local tilt of the center line.

According to a preferred method, the detection of the center points (of the vertebrae) is performed with a trained machine learning algorithm, that is especially a deep neural network. Such algorithm could be trained on images showing a spine with the relevant vertebrae as training data with an information about segmented vertebrae together with their center points as ground truth. A preferred algorithm is a neural network, typically used for image processing, especially a convolutional network.

According to a preferred method, the center line is constructed as a smooth line or is smoothed after a preliminary construction. This has the advantage that it is optimized to follow the center line of the real spine, since its course is smooth. Suitable techniques to smoothen a line are well known in the art.

According to a preferred method, a segmentation of an endplate of a reference vertebra is determined by using a trained machine learning algorithm, that is especially a deep neural network. Such algorithm could be trained on images showing a spine with segmented vertebrae or only segmented vertebrae as training data with an information about the position of endplates of the segmented vertebrae as ground truth. A preferred algorithm is a neural network typically used for image processing, especially a convolutional network. Depending on the use there could be used one algorithm for both endplates or one algorithm specially trained to find upper endplates and another algorithm specially trained to find lower endplates.

According to a preferred method, the segmentation of an endplate is determined by a detection of a certain number (e.g. six) of point landmarks on the endplate followed by a linear fit. Alternatively or additionally, the segmentation of an endplate is determined by a landmark regression approach that assigns probabilities for each pixel in the image that it belongs to the endplate of that vertebra, especially also followed by a fit. It is preferred that in the course of a pre-processing step, a region of interest is defined around the reference vertebra which is used to crop the image before analysis.

Concerning a preferred device, the detection of landmarks could be realized in a first module ("landmark module") and the post-processing of landmarks is realized in a second module ("post-processing module").

Thus, the center-point unit and especially also the center-line unit could be realized in a landmark module together with the segmentation unit or at least a part of this unit. The aim of these units is typically the determination of landmarks and could be realized with one single (deep) neural network or a neural network for each unit (and in the case of the segmentation unit also separate (deep) neural networks for each endplate).

The line-tilt unit, the max-min unit and a unit to realize an endplate point fit could be realized in a post-processing module, wherein this endplate point fit unit may be a part of the segmentation unit. Thus, the segmentation unit may have a two-part form. The first part is a detector for recognizing the respective endplates (e.g. a number of points of the endplates) and the second part may be a unit performing an endplate point fit. The first part could be part of the first module and the second part could be part of the second module.

A third module may comprise the angel-determination unit and especially also a unit designed for calculate a coronal/sagittal balance.

According to a preferred method, steps d) to g) are repeated with further reference vertebrae and preferably further local positive and negative tilt-maxima and/or a different section of the center line. It is preferred that further reference vertebrae are chosen that are nearest to further local positive or negative tilt-maxima of the center line or nearest the former reference vertebrae. It should be noted that in the case that there are more than one positive or more than one negative tilt-maxima, the largest tilt-maxima are chosen at first and after that during a further cycle another (especially the next smaller) tilt-maximum is used. Preferably (to be considered), a curve of the spine the Cobb angle should be >10 degrees. If there are several peaks on the centerline tilt function, it is preferred that adjacent peaks are chosen for min and max determinations.

According to a preferred method, an angle is calculated based on the segmentation of the endplates in addition with an intermediate angle measured from the local tilt of the center line at the position of the endplates. This has the advantage that a sanity check of the vertebral tilt ("geometrical condition of the endplate") could be performed. This tilt is highly correlated to the tilt of the centerline. In the case there is a high deviation, typically the values from the center line tilt are more trustworthy.

According to a preferred method, additionally a coronal or sagittal balance is calculated based on the center points of the vertebrae, especially based on the center line. The coronal balance is preferably measured as the horizontal distance between the center points of C7 and S1 on a coronal spine image. The sagittal balance is preferably measured as the horizontal distance between the center point of C7 and the posterior-superior corner of S1 on a sagittal spine image. The device preferably comprises a distance-determination unit designed to calculate the coronal or sagittal balance.

According to a preferred method, in step g), a Cobb-like angle between the upper and lower endplates of the reference vertebrae is calculated. Alternatively, an angle quantifying thoracic kyphosis, an angle quantifying lumbar lordosis or another angle in the sagittal plane which is a common spinal measurement between the upper and lower endplates of the reference vertebrae is calculated.

According to a preferred method, step g) comprises the sub steps (for each endplate):

determining an E-angle measured via the endplate orientation, determining a L-angle that is the intermediate angle measured from the local center line tilt at the intersection of the center line and the endplate, comparing the E-angle with the L-angle.

The "check" is done individually for the upper endplate (cranial vertebral body) and the lower endplate (caudal vertebral body).

It is preferred that in the case when the E-angle deviates by more than a predefined value from the L-angle, a corrected C-angle is determined such that the C-angle is closer to the L-angle than the E-angle. The C-angle is then used as determined angle of the method and is outputted. This advantageously increases the robustness of the method.

Thus, the angle measured via the endplate (E-angle) is compared with the intermediate angle measured from the local center line tilt (L-angle). These two angles are highly correlated and should not deviate too much. If the E-angle deviates by more than a certain value from the L-angle, then its value is here adjusted such that the resulting C-angle is closer to the L-angle. It is assumed that the L-angle can be determined more robust compared to the E-angle.

According to a preferred method, the corrected C-angle is calculated from the E-angle and the L-angle by using a weight function w by the formula: C-angle=w·L−angle+(w−1)·E-angle.

It is preferred that w is determined with an absolute value d=abs(E-angle−L-angle) of the difference between E-angle and L-angle with, and predefined scalar values a and b by the sigmoid function w=1/(1+exp(−a·(d−b))) or otherwise written:

$$w = \frac{1}{1 + e^{-a(d-b)}}.$$

The parameters a and b are here just scalar values defining the shape of the sigmoid function w. The value b can be interpreted as the acceptable deviation between E-angle and L-angle.

In a preferred embodiment according to the present invention, components of the device are part of a data-network, wherein preferably the data-network and a medical imaging system (i.e. an X-ray system which provides data of the image) are in data-communication with each other, wherein the data-network preferably comprises parts of the internet and/or a cloud-based computing system, wherein preferably the device according an embodiment of the present invention or at least a number of components of this device is realized in this cloud-based computing system. For example, the components of the system are part of a data-network, wherein preferably the data-network and a medical imaging system which provides the image data are in communication with each other. Such a networked solution could be implemented via an internet platform and/or in a cloud-based computing system.

The method may also include elements of "cloud computing". In the technical field of "cloud computing", an IT infrastructure is provided over a data-network, e.g. a storage space or processing power and/or application software. The communication between the user and the "cloud" is achieved via data interfaces and/or data transmission protocols.

In the context of "cloud computing", in a preferred embodiment of the method according to one or more example embodiments of the present invention, provision of data via a data channel (for example a data-network) to a "cloud" takes place. This "cloud" includes a (remote) computing system, e.g. a computer cluster that typically does not include the user's local machine. This cloud can be made available in particular by the medical facility, which also provides the medical imaging systems. In particular, the image acquisition data is sent to a (remote) computer system (the "cloud") via a RIS (Radiology Information System) or a PACS (Picture Archiving and Communication System).

Within the scope of a preferred embodiment of the system according to one or more example embodiments of the present invention, the abovementioned units (center-point unit, center-line unit, line-tilt unit, max-min unit, segmentation unit, angel-determination unit) Are present on the "cloud" side. A preferred system further comprises, a local computing unit connected to the system via a data channel (e.g. a data-network, particularly configured as RIS or PACS). The local computing unit includes at least one data receiving interface to receive data. Moreover, it is preferred if the local computer additionally has a transmission interface in order to send data to the system.

One or more example embodiments of the present invention provide a method that can automatically determine a Cobb-angle-like angle which is robust against local outliers in endplate orientations and satisfies the need to report a value that is measured based on accepted anatomical landmarks. It should be noted that formally the method does not measure the traditional Cobb angle but as an intermediate step uses the local tilt (angle) of the smoothed center line to find the reference vertebrae. However, from a clinical perspective this approach is considering the global curvatures in a natural way and is a benefit for the characterization of the spinal curvature.

BRIEF DESCRIPTION OF THE DRAWINGS

Objects and features of the present invention will become apparent from the following detailed descriptions considered in conjunction with the accompanying drawings. It is to be understood, however, that the drawings are designed solely for the purposes of illustration and not as a definition of the limits of the present invention.

In the diagrams, like numbers refer to like objects throughout. Objects in the diagrams are not necessarily drawn to scale.

DETAILED DESCRIPTION

Figure 1:
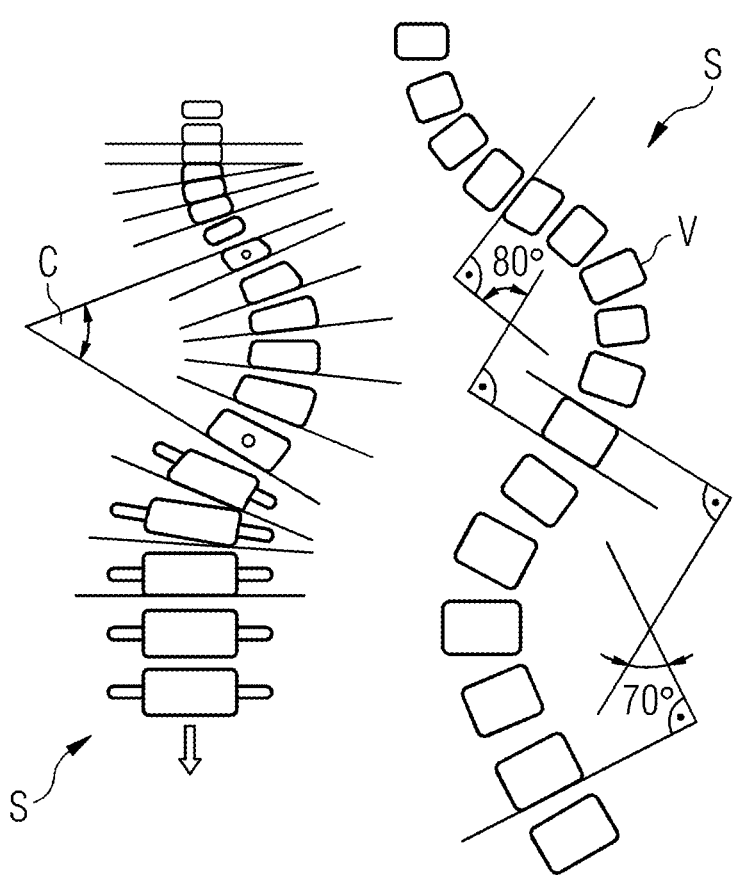
FIG. 1 shows the curvature of a spine in a coronal plane and in a sagittal plane and the definition of a Cobb angle.

FIG. 1 shows the curvature of a spine S with its vertebrae V in a coronal plane: C-shaped spine (left) and S-shaped spine (right). The Cobb angle C according to the traditional definition is the angle between most tilted vertebrae above and below the apex of the curve (left). It should be noted that for the S-shaped spine one can measure two Cobb angles. The angles are measured between the superior endplate of the upper and the inferior endplate of the lower end vertebra. Thus, the Cobb angle depends on the local endplate orientation and neglects important parts of the curve characteristics.

Figure 2:
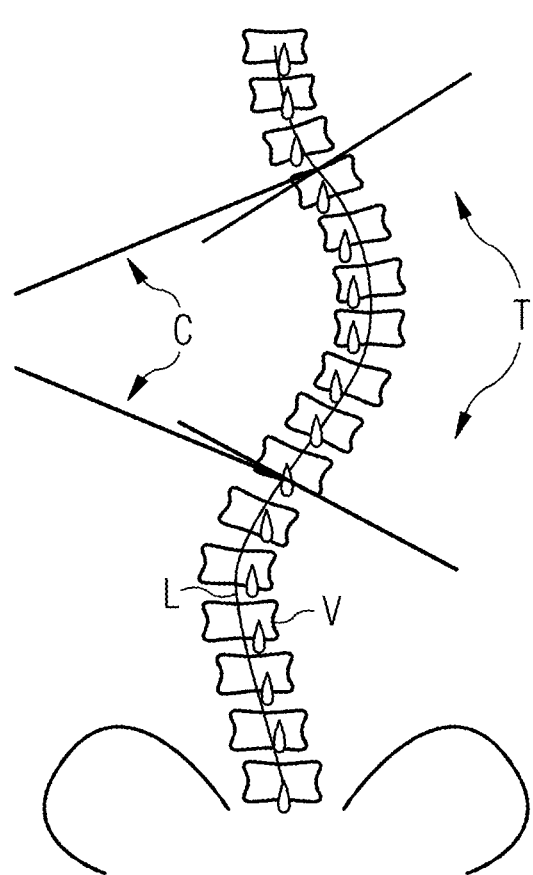
FIG. 2 shows the curvature of a spine in a coronal plane.

FIG. 2 shows the curvature of a spine S in a coronal plane. One can see the Cobb angle as determined in FIG. 1 and the tilt T of the center line L of the vertebrae V of the spine. It can be seen that the Cobb angle and the angle resulting from the tilts T of the center line at the position of the respective endplates are highly correlated to each other, but nevertheless slightly differ from each other.

Figure 3:
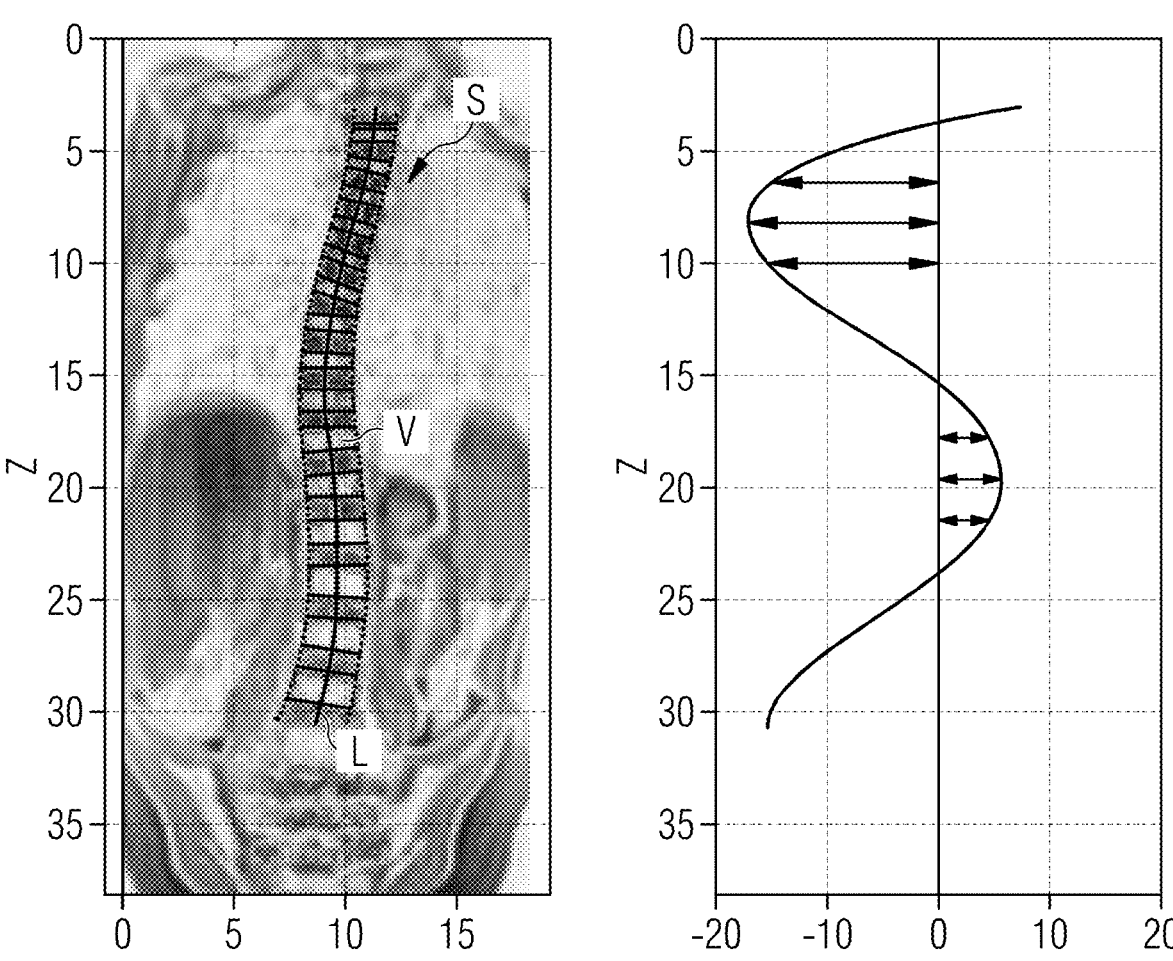
FIG. 3 shows the curvature of a spine in a coronal plane and a corresponding angle function.

FIG. 3 shows the curvature of a spine S in a coronal plane (left) and a corresponding angle function (right). The angle function is the first derivative of the center line L of the spine S in respect to the Z-coordinate Z. The spinal center line L is also designated as "composite structural curve" and the angle function is directly computed from this curve. The spinal curvature can be determined by finding the vertebral center points, constructing a smooth center line through the center points and using the curvatures of the centerline to determine Cobb-angle-like angles.

Mathematically, this involves computing an "angle function" (the tilt of the center line vs. the horizontal line at every height point and taking the negative and positive maxima as reference points for the measurement. This concept is also referred to as the "analytical Cobb angle".

Figure 4:
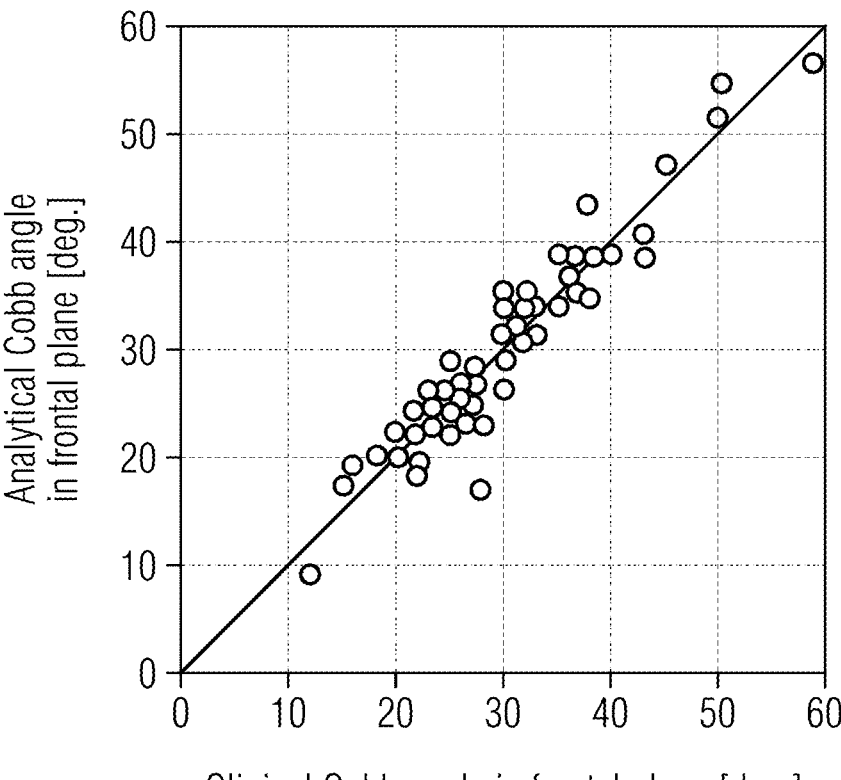
FIG. 4 shows the relation of the Cobb angle of FIG. 1 versus the analytical Cobb angle of FIG. 3.

FIG. 4 shows the relation of the (traditional) Cobb angle C of FIG. 1 versus the analytical Cobb angle C of FIG. 3. One can see that the relation is close, but not 100 percent identical.

Figure 5:
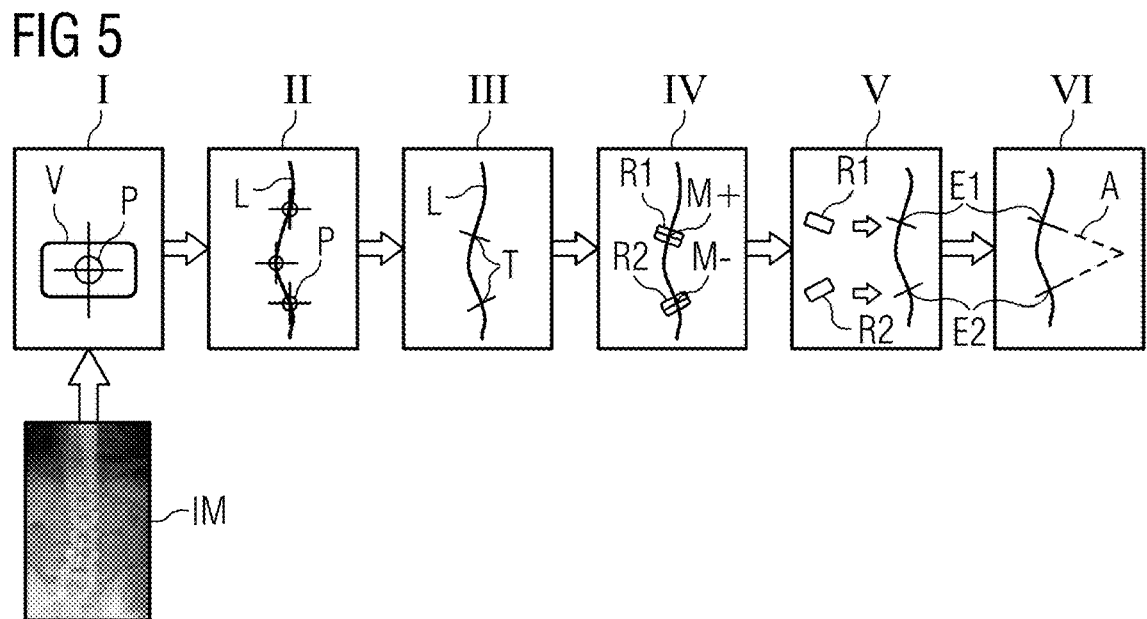
FIG. 5 shows a block diagram of the process flow of a preferred method according to one or more example embodiments of the present invention.

FIG. 5 shows a block diagram of the process flow of a preferred method, according to one or more example embodiments of the present invention, for automatically determining spine deformation from an image IM showing a number of vertebrae V of the spine S (see e.g. FIG. 3).

The method may be divided into two parts. The first part (steps I to IV) concerns finding reference vertebrae R1, R2 based on local center line tilts T. The second part (steps V and VI) concerns computing an angle based on an upper/lower endplate tilt T of these reference vertebrae R1, R2.

In step I, the center points P of a number of vertebrae V shown in the image IM are detected. In practice, an algorithm (a trained deep neural network, "model A") detects the center points P of the vertebrae V (from C1 to S1) in the shown coronal X-ray image IM. In the case not all vertebrae V are visible, only the visible center points P are detected.

In step II, a (smooth) center line L is constructed based on the detected center points P. In this example, the center line is computed using smoothing splines.

In step III, a local tilt T is computed at points (each point) along the center line L. This can be achieved by computing the first derivative along the curve.

In step IV, the positive and negative tilt-maxima M+, M− of the local tilt T are determined and two reference vertebrae R1, R2 having their center points P closest to the determined tilt-maxima M+, M− are selected.

In step V, segmentations of the endplates E1, E2 of the reference vertebrae R1, R2 are determined. This is the segmentation of the upper endplate E1 of the cranial reference vertebra R1 and the segmentation of the lower endplate E2 of the caudal reference vertebra R2.

The more cranial reference vertebra R1 can be analyzed by a second algorithm (trained deep neural network, "model B1") that detects the upper endplate E1 of this reference vertebra R1. This can be implemented by a detection of a certain number (e. g. six) of point landmarks on the endplate E1 followed by a linear fit, for example. Another implementation could be a landmark regression approach that assigns probabilities for each pixel in the image that it belongs to the endplate E1 of that reference vertebra R1 (also followed by a fit). As preprocessing step, a region of interest can be defined around the reference vertebra R1 which is used to crop the image IM before analysis by the second algorithm.

The same action is carried out for the second, more caudal, reference vertebra R2 to find the lower endplate E2 using a third algorithm (trained deep neural network, "model B2"). The second and third algorithms model B1 and B2 could be separately trained networks or be the same trained network.

The three models for recognizing elements in the image IM (model A for recognizing the vertebrae V and their center points P and models B1 and B2 for recognizing endplates E1, E2) could be hosted in a special "landmark module", e.g. a powerful computing unit, especially in a cloud.

In step VI, the angle A between the upper endplate E1 and lower endplate E2 of the reference vertebrae R1, R2 is computed and outputted. Based on the orientations of the upper and lower endplates E1, E2 a Cobb-like angle could be computed from the image IM.

If the spine has an S-shape usually more than one angle A should be reported (typically two, sometimes three). In this case steps IV to VI are repeated for different segments along the curve or for different maxima M+, M− and/or a different section of the center line L.

Figure 6:
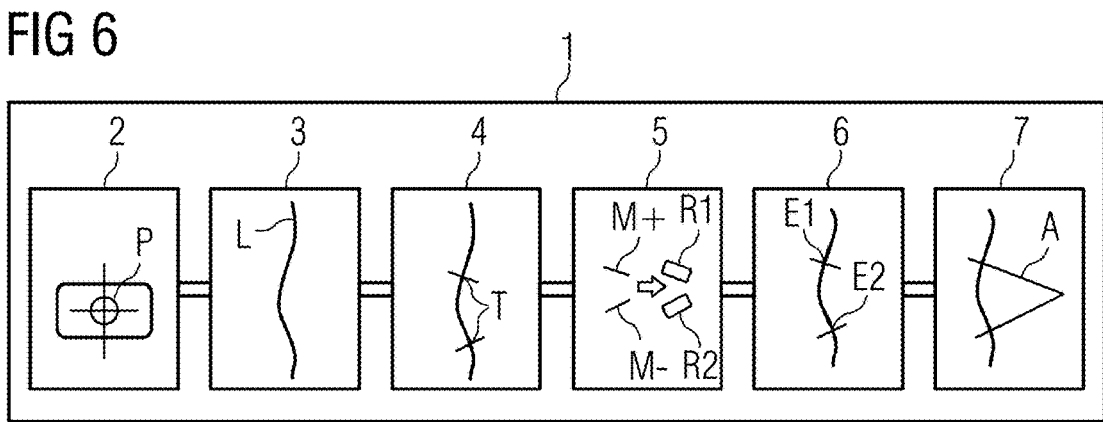
FIG. 6 shows a device according to one or more example embodiments of the present invention.

FIG. 6 shows a device 1 according, to one or more example embodiments of the present invention, for automatically determining spine deformation from an image IM showing a number of vertebrae V of the spine S with a method as shown in FIG. 5. The device 1 comprises the following components:

A center-point unit 2 designed for detecting the center points P of a number of vertebrae V shown in the image IM. This unit may comprise a (deep) neural network specially trained for this purpose.

A center-line unit 3 designed for constructing a center line L based on the detected center points P. This unit may comprise a conventional algorithm that is designed to construct a smooth line based on splines through the detected center points P.

A line-tilt unit 4 designed for computing a local tilt T at points along the center line L. This unit may compute the first derivative of the center line L in respect to its length or the Z-axis (height of the patient).

A max-min unit 5 designed for determining the positive and negative tilt-maxima M+, M− of the local tilt T and select two reference vertebrae R1, R2 having their center points P closest to the determined tilt-maxima M+, M−. This can be easily achieved by looking at local maxima of the first derivative or by calculating the second derivative and look for zero-values there.

A segmentation unit 6 designed for segmenting an upper endplate E1 of the cranial reference vertebra R1, and designed for segmenting a lower endplate E2 of the caudal reference vertebra R2. This could be achieved by above described models B1 and B2 (or one single model B). Thus, this unit may also comprise a (deep) neural network or two (deep) neural networks specially trained for this purpose.

An angel-determination 7 unit designed for computing an angle A between the upper endplate E1 and lower endplate E2 of the reference vertebrae R1, R2 and outputting this angle A. Knowing the tilt of the endplates and their position (i.e. the geometrical conditions), the angle A can easily be calculated, e.g. forming 2D-vectors with the tilt of the endplates E1, E2 at the positions of the endplates E1, E and calculating the angle A between these two vectors.

Figure 7:
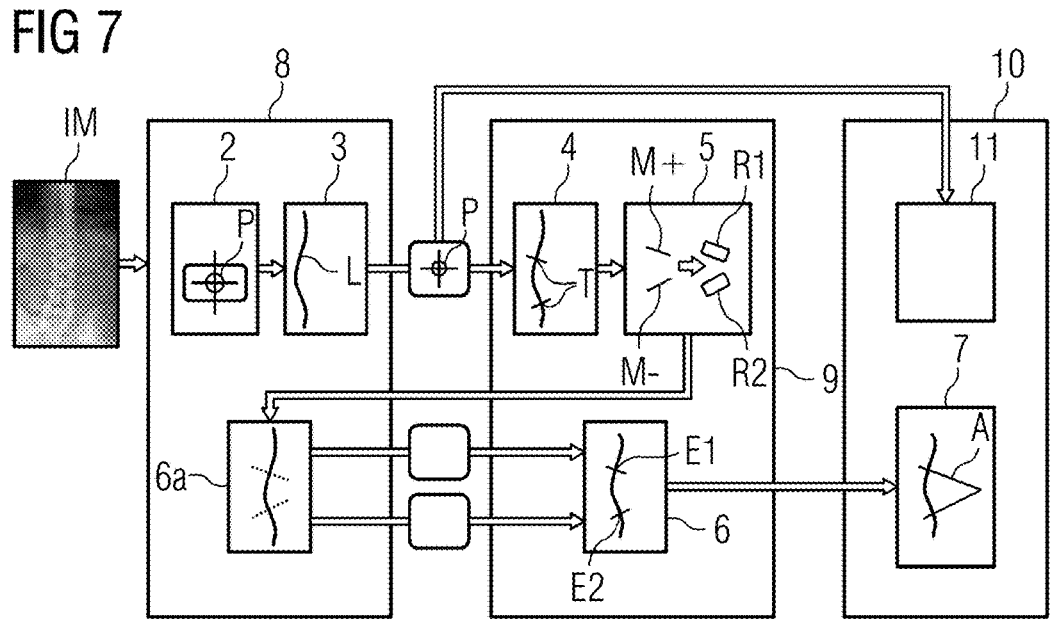
FIG. 7 illustrates the workflow of one or more example embodiments of the present invention.

FIG. 7 illustrates the workflow of one or more example embodiments of the present invention. Here, the units of the device 1 described in FIG. 6 are distributed in three modules: a landmark module 8, a post-processing module 9 and a measurement module 10.

The center-point unit 2 and especially also the center-line unit 3 are here part of the landmark module 8 together with an endplate unit 6a (performing an endplate point fit in order to segment endplates E1, E2). The aim of these units is typically the determination of landmarks and could be realized with one single (deep) neural network or a neural network for each unit (and in the case of the endplate unit 6a, also separate (deep) neural networks for each endplate E1, E2). The landmark module 8 could be arranged in a cloud receiving the image IM and providing the results (i.e. segmented image IM with vertebrae V and center points P as well as recognized endplates E1, E2). The endplate unit 6a may be a unit of the segmentation unit 6 or the center point unit 2. Thus, the segmentation unit 6 may be distributed in both modules 8, 9. The first part of the segmentation unit 6 is the endplate unit 6a designed for recognizing the respective endplates (e.g. a number of points of the endplates) and the second part is a unit performing an endplate point fit after receiving the points generated by the first part.

From the landmark module 8, the recognized center points P of the vertebrae V (e.g. their coordinates) are sent to the post processing module 9. Also, the landmarks, e.g. six points characterizing the geometrical condition of the endplates E1, E2, are sent to the post-processing module 9. Thus, in the case, where the landmark module 8 is realized in a cloud, the image IM has to be uploaded to the cloud that may be a large dataset, but the results received from the cloud may be small datasets (coordinates only).

The line-tilt unit 4, the max-min unit 5 and the segmentation unit 6 could be realized in the post-processing module 9.

The measurement module 10 comprises the angel-determination unit 7. In this figure also the computation of the coronal balance is included. The coronal balance is measured as the horizontal distance between the center points of C7 and S1. Thus, this module could also comprise a distance-determination unit 11.

All these modules could be realized in a cloud.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been disclosed in the form of preferred embodiments and variations thereon, it will be understood that numerous additional modifications and variations could be made thereto without departing from the scope of the present invention. For the sake of clarity, as mentioned similarly above, it is to be understood that the use of "a" or "an" throughout this application does not exclude a plurality, and "comprising" does not exclude other steps or elements. The expression "a number of" means "at least one". The mention of a "unit" or a "device" does not preclude the use of more than one unit or device.

What is claimed is:

1. A method for automatically determining spine deformation from an image showing a number of vertebrae of a spine of a patient, the method comprising:

detecting first center points of the number of vertebrae shown in the image;

constructing a center line based on the first center points;

computing a local tilt at points along the center line;

determining positive and negative tilt-maxima of the local tilt;

selecting two reference vertebrae having corresponding center points closest to the positive and negative tilt-maxima, the two reference vertebrae being among the number of vertebrae, and the corresponding center points being among the first center points;

segmenting an upper endplate of a cranial reference vertebra among the two reference vertebrae;

segmenting a lower endplate of a caudal reference vertebra among the two reference vertebrae;

computing a first angle between the upper endplate and the lower endplate, the first angle quantifying a degree of a deformity of the spine, the computing the first angle including calculating the first angle based on an intermediate angle, the segmenting the upper endplate and the segmenting the lower endplate, and the intermediate angle being measured from the local tilt of the center line at a position of at least one of the upper endplate or the lower endplate; and outputting the degree of the deformity of the spine as represented by the first angle, wherein the image is a medical image of the spine of the patient produced by a corresponding medical imaging device.

2. The method according to claim 1, wherein the image comprises a view on a coronal plane or a sagittal plane of the patient.

3. The method according to claim 1, wherein the detecting the first center points is performed with a trained machine learning algorithm.

4. The method according to claim 3, wherein the trained machine learning algorithm is a deep neural network.

5. The method according to claim 1, wherein the center line is constructed as a smooth curve or is smoothed after a preliminary construction.

6. The method according to claim 1, wherein at least one of the segmenting the upper endplate or the segmenting the lower endplate is performed using a trained machine learning algorithm.

7. The method according to claim 6, wherein the trained machine learning algorithm is a deep neural network.

8. The method according to claim 1, wherein at least one of the segmenting the upper endplate includes detecting a number of point landmarks on the upper endplate, and performing at least one of a linear fit or a landmark regression approach that assigns probabilities for each pixel in the image to the upper endplate of the cranial reference vertebra, or the segmenting the lower endplate includes detecting a number of point landmarks on the lower endplate, and performing at least one of a linear fit or a landmark regression approach that assigns probabilities for each pixel in the image to the lower endplate of the caudal reference vertebra.

9. The method according to claim 8, wherein the at least one of the segmenting the upper endplate or the segmenting the lower endplate further comprises:

defining a region of interest around a first reference vertebra that is used to crop the image before analysis, the first reference vertebra being among the two reference vertebrae.

10. The method according to claim 1, further comprising:

repeating the determining, the segmenting the upper endplate, the segmenting the lower endplate and the computing the first angle based on further reference vertebrae.

11. The method according to claim 10, wherein the repeating is performed with at least one of a different section of the center line or further positive and negative tilt-maxima.

12. The method according to claim 1, further comprising:

calculating a coronal balance or a sagittal balance based on the first center points.

13. The method according to claim 12, wherein the calculating calculates the coronal balance or the sagittal balance based on the center line;

the coronal balance is measured as a horizontal distance between center points of C7 and S1 on a coronal spine image, center points of C7 and S1 being among the first center points; and the sagittal balance is measured as a horizontal distance between a center point of C7 and a posterior-superior corner of S1 on a sagittal spine image.

14. The method according to claim 1, wherein the first angle is a Cobb-like angle, an angle quantifying thoracic kyphosis, an angle quantifying lumbar lordosis, or another angle in a sagittal plane.

15. The method according to claim 1, wherein the computing the first angle comprises:

determining an E-angle that is measured based on the upper endplate and the lower endplate;

determining a L-angle as the intermediate angle measured from the local tilt;

comparing the E-angle with the L-angle; and determining a corrected C-angle in response to the E-angle deviating from the L-angle by more than a threshold value, the corrected C-angle being closer to the L-angle than the E-angle.

16. The method according to claim 15, wherein the determining the corrected C-angle comprises:

calculating the corrected C-angle based on the E-angle, the L-angle and a weight function w according to a formula given by $$C\text{-angle} = w \cdot L\text{-angle} + (w-1) \cdot E\text{-angle}.$$

17. The method according to claim 16, wherein the weight function w is given by $$w = 1/(1 + \exp(-a \cdot (d-b)));$$

$d = \mathrm{abs}(E\text{-angle} - L\text{-angle})$; and a and b are scalar values.

18. A non-transitory computer program product comprising a computer program that is loadable into a computing system, the computer program including program elements that, when executed by the computing system, cause the computing system to perform the method of claim 1.

19. A non-transitory computer-readable medium storing program elements that, when executed by at least one processor, cause the at least one processor to perform the method according to claim 1.

20. The method of claim 1, wherein the medical image is an X-ray image, a computed tomography image, an ultrasound image or a magnetic resonance image, the computed tomography image including multi-planar reformatted slices.

21. The method according to claim 1, wherein the detecting the first center points, the segmenting the upper endplate and the segmenting the lower endplate are performed using at least one trained machine learning algorithm.

22. A device for automatically determining spine deformation from an image showing a number of vertebrae of a spine of a patient, the device comprising:

processing circuitry configured to detect first center points of the number of vertebrae shown in the image, construct a center line based on the first center points, compute a local tilt at points along the center line, determine positive and negative tilt-maxima of the local tilt, select two reference vertebrae having corresponding center points closest to the positive and negative tilt-maxima, the two reference vertebrae being among the number of vertebrae, and the corresponding center points being among the first center points, segment an upper endplate and a lower endplate using at least one trained machine learning algorithm, the upper endplate being of a cranial reference vertebra among the two reference vertebrae, and the lower endplate being of a caudal reference vertebra among the two reference vertebrae, calculate a first angle between the upper endplate and the lower endplate based on an intermediate angle, the segmentation of the upper endplate and the segmentation of the lower endplate, the intermediate angle being measured from the local tilt of the center line at a position of at least one of the upper endplate or the lower endplate, and the first angle quantifying a degree of a deformity of the spine, and output the degree of the deformity of the spine as represented by the first angle, wherein the image is a medical image of the spine of the patient produced by a corresponding medical imaging device.

23. A device for automatically determining spine deformation from an image showing a number of vertebrae of a spine of a patient, the device comprising:

a memory storing computer executable instructions; and at least one processor configured to execute the computer executable instructions to cause the device to detect first center points of the number of vertebrae shown in the image, construct a center line based on the first center points, compute a local tilt at points along the center line, determine positive and negative tilt-maxima of the local tilt, select two reference vertebrae having corresponding center points closest to the positive and negative tilt-maxima, the two reference vertebrae being among the number of vertebrae, and the corresponding center points being among the first center points, segment an upper endplate of a cranial reference vertebra among the two reference vertebrae, segment a lower endplate of a caudal reference vertebra among the two reference vertebrae, calculate a first angle between the upper endplate and the lower endplate based on an intermediate angle, the segmentation of the upper endplate and the segmentation of the lower endplate, the intermediate angle being measured from the local tilt of the center line at a position of at least one of the upper endplate or the lower endplate, and the first angle quantifying a degree of a deformity of the spine, and output the degree of the deformity of the spine as represented by the first angle, wherein the image is a medical image of the spine of the patient produced by a corresponding medical imaging device.

* * * * *